United States Patent
Beaussoubre et al.

(10) Patent No.: US 8,354,369 B2
(45) Date of Patent: Jan. 15, 2013

(54) SPRAYABLE PERFUME WITH AN IMPROVED TENACITY

(75) Inventors: Pascal Beaussoubre, Collonges sous Saleve (FR); Thierry Stora, Thoiry (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/352,948

(22) Filed: Jan. 18, 2012
(Under 37 CFR 1.47)

(65) Prior Publication Data
US 2012/0114580 A1    May 10, 2012

Related U.S. Application Data

(63) Continuation of application No. 11/266,060, filed on Nov. 2, 2005, now abandoned, which is a continuation of application No. PCT/IB2004/001603, filed on May 3, 2004.

(30) Foreign Application Priority Data

May 7, 2003    (EP) .................................... 03010264

(51) Int. Cl.
*A61Q 13/00*    (2006.01)
(52) U.S. Cl. .......................................................... 512/2
(58) Field of Classification Search ........................ 512/2
See application file for complete search history.

(56) References Cited

U.S. PATENT DOCUMENTS

| | | | |
|---|---|---|---|
| 3,506,674 A | 4/1970 | Berger | 260/294.8 |
| 3,567,118 A * | 3/1971 | Shepherd et al. | 239/6 |
| 3,900,520 A | 8/1975 | Schenk et al. | 260/586 R |
| 4,482,537 A * | 11/1984 | El-Menshawy et al. | 424/59 |
| 5,223,251 A | 6/1993 | Nichols | 424/69 |
| 5,420,104 A | 5/1995 | Holzner et al. | 512/2 |
| 5,686,405 A | 11/1997 | Lebreton et al. | 512/2 |
| 6,083,900 A | 7/2000 | Auguste et al. | 512/2 |
| 6,126,930 A | 10/2000 | Dubois et al. | 424/73 |
| 6,172,037 B1 | 1/2001 | Perring et al. | 512/2 |
| 6,183,766 B1 | 2/2001 | Sine et al. | 424/405 |
| 2003/0147926 A1 | 8/2003 | Ebert et al. | 424/400 |

FOREIGN PATENT DOCUMENTS

| | | |
|---|---|---|
| EP | 0 181 401 B1 | 5/1986 |
| EP | 0 700 677 B1 | 3/1996 |
| EP | 0 857 481 B1 | 8/1998 |
| GB | 1 602 747 A | 11/1981 |

OTHER PUBLICATIONS

Carbopol® Polymers—Personal Care—The Lubrizol Corporation, http://www.lubrizol.com/PersonalCare/Products/Carbopol/default.html (Dec. 5, 2011).

Pemulen™ Polymers—Household, Institutional and Industrial—The Lubrizol Corporation, http://www.lubrizol.com/Household/Pemulen/default.html (Dec. 5, 2011).

International Search Report, Application No. PCT/IB2004/001603, dated Jul. 6, 2004.

* cited by examiner

*Primary Examiner* — Ling Choi
*Assistant Examiner* — Lanee Reuther
(74) *Attorney, Agent, or Firm* — Wintson & Strawn LLP (57) ABSTRACT

An alcoholic perfume solution with an improved tenacity when applied onto a surface is described. The solution contains an effective amount of a single polymer capable of extending the diffusion of perfuming ingredients in the air.

7 Claims, 5 Drawing Sheets

SPRAYABLE PERFUME WITH AN IMPROVED TENACITY

CROSS-REFERENCE TO RELATED APPLICATIONS

This application is a continuation of application Ser. No. 11/266,060 filed Nov. 2, 2005, which is a continuation of International Application PCT/IB2004/001603 filed May 3, 2004, the entire content of each of which is expressly incorporated herein by reference thereto.

TECHNICAL FIELD

The present invention relates to the field of perfumery. It concerns more particularly a novel perfume solution, transparent and susceptible of being sprayed, characterised by the presence in its composition of an effective amount of a single polymer, capable of decreasing the spreading area of the perfume composition when applied on a surface. Said novel composition proved capable of extending the diffusion of the perfuming ingredients from a surface into the surrounding environment, thus prolonging the organoleptic effect of a perfume when applied onto a surface such as the skin.

BACKGROUND ART

It is well known in the art of fine fragrance that, when an alcoholic perfume is applied onto the skin, the volatile top notes are stripped preferentially by ethanol evaporation while the more heavy notes exhibit superior tenacity, i.e., they are released from the skin over a longer period of time. As a consequence, many attempts have been made to improve the tenacity or extend the diffusion time of a perfume intended for an application on a support such as the skin, particularly as regards the most volatile ingredients of the fragrance. The use of so-called "perfume fixatives" in perfume formulations has been widely described and usually consists in adding to a perfume composition one or more ingredients capable of chemically modifying the structure of the composition itself, so as to retain the perfuming ingredients in the structure and slow down their release into the ambient air.

In particular, some patent literature discloses the use of ingredients which have the effect of gelling or even solidifying the compositions to which they are added, thus slowing down the diffusion in the air of particularly volatile ingredients. For instance, European patent application EP181401 describes a gelatinised perfume formed by mixing a mixture formed by adding a perfume oil to an alcohol solution containing from 1 to 5% of hydroxypropylcellulose, with a saturated solution of dibenzylidenesorbital in N-methyl-2-pyrrolidone, to form a gel-like solid mixture in which the alcohol is inactivated and thus the fragrance persistent. In this process, the volatility of the alcohol is reduced by the incorporation of hydroxypropylcellulose and, at the same time, the gelatinisation activated by the presence of dibenzylidenesorbitol allows to control the scattering of the fragrance. On the other hand, European patent application EP 857481 describes a composition, in the form of a gel, associating an organosiloxane compound together with a hydrocarbonated, siliconated or fluorinated oil. These additives are added in large quantities and contribute to the formation of a gel.

These documents, disclosing compositions that retain the perfume by way of gelatinisation or solidification, do not allow to prepare perfumes of low viscosity capable of being sprayed.

European patent application EP 700677 approaches the same problematic of fixing a perfume and/or extending the perfume release from a dermatological or cosmetic composition. More particularly, said document describes the use in such compositions of a vegetable compound consisting of a vegetable extract combined with a vegetable gum. In that disclosure, it is mentioned that a solvent such as ethanol must be present in low quantity in the composition to avoid the release of an important amount of perfume all at once. This limitation prevents such compositions from being used in the field of fine perfumery, wherein perfume solutions are essentially based on the use of very large quantities of alcohol in order to solubilize the perfuming ingredients.

On the other hand, U.S. Pat. No. 6,172,037 discloses a perfume fixative constituted by the association of three particular ingredients, namely polyvinylpyrrolidone, hydroxypropyl cellulose and a non volatile hydrophobic oil, the two first ingredients being present in quantities below 0.5% by weight of the perfume-containing product. The perfumes thus prepared are particularly useful in applications such as deodorants, deo-colognes and antiperspirants. In this document, the combination of the three ingredients is essential to enhance the fragrance life, but the amounts of the latter are limited, as they are discernible by the user when used in high quantities. All the examples given in said document are perfume formulations for an intended use in deodorant type applications and thus comprise a limited amount of perfume, usually from 1 to 2% by weight of perfume relative to the total weight of the final composition. Therefore, it is very likely that the disclosed fixative ingredients are not suitable for fine fragrance or perfume formulations that comprise higher quantities of perfume, as the fixative would then have to be used in higher quantities and would thus be detectable by the user.

Therefore, in view of the existing prior art related to "fixative ingredients" capable of extending the diffusion of volatile ingredients present in perfumes, the compositions provided up-to-date still have many limitations and, in particular, none of the prior art solutions are suitable for an application in fine perfumery, i.e., applications wherein the perfume formulation must be transparent, sprayable, comprises a high quantity of alcohol and a high quantity of perfuming ingredients. The present invention now provides a solution to the above mentioned problems.

SUMMARY OF THE INVENTION

The present invention concerns a transparent perfume solution based essentially on the presence of high quantities of alcohol, a high amount of perfuming ingredients and water, i.e., a formulation typically used in fine perfumery, together with an effective amount of a single active ingredient which allows to extend the diffusion of the perfume over time, in particular of the volatile or top notes, when applied on any kind of surface, in particular when applied onto the skin. Moreover, the perfume composition of the invention has a more linear release profile and thus the perfume remains more balanced over time.

The invention relates to a transparent sprayable perfume solution, essentially comprising from 50 to 99% by weight of ethanol; from 0.5 to 50% by weight of a perfuming ingredient or composition; and from 0.5 to 50% by weight of water, and an effective amount of a single polymer selected from the group consisting of a linear or cross-linked (meth-) acrylic acid homo-polymer, a linear or cross-linked (meth-) acrylate copolymer, an ammonium acryloyldimethyltaurate homo- or copolymer and a polyethylene oxide or a derivative thereof, the weight percents being relative to the total weight of the composition. Said perfume solution is thus characterised by the presence of an effective amount of a single polymer capable of decreasing the spreading area of the composition when applied onto a surface.

The present invention provides a novel solution to the very well known problem of extending the diffusion of perfumes from a support. This solution suits many types of applications, and particularly perfume formulations intended for an use in fine perfumery, such as perfumes and eaux de toilette, for which fixative ingredients known up-to-date were not found to be appropriate for the reasons explained above in the Background Art.

Other aspects and advantages of the present invention are disclosed in the description as well as in the examples that follow.

DETAILED DESCRIPTION OF THE PREFERRED EMBODIMENTS

The solution provided by the invention does not lie, as disclosed in the prior art, on the particular interactions between the fixative ingredients and the perfuming ingredients which depend mostly on the chemical nature of the fixative. In fact, the active ingredient added to the perfume solution according to the present invention is capable of modifying a physical property of the liquid, namely its spreading capability measured by the so-called "spreading area" when applied onto a surface, with the effect of extending the diffusion of the perfume, while advantageously keeping good sprayability.

The "spreading area" is a parameter well known to a skilled person in the art, measurable at the interface between a solid and a liquid. When a liquid is brought into contact with a solid surface, in case of partial wetting, a droplet with a certain contact angle is formed on the solid surface and the "spreading area" of the liquid corresponds to the contact area existing between the liquid droplet and the solid surface. The contact area is circular on an homogeneous substrate and the measure of the diameter of the contact area therefore allows to calculate the spreading area of a liquid onto a surface.

Now, in the present invention, once a droplet of a perfume solution according to the invention is applied onto a surface, such as the skin for instance, the spreading area of the liquid is unexpectedly reduced by comparison with the area measured for an identical composition but free of the single polymer characterising the invention. As a consequence, in a solution according to the invention, after the evaporation of ethanol, the perfume is concentrated in a smaller surface and thus evaporates more slowly than in a classical composition. Therefore, it has been unexpectedly discovered, as shown by the headspace measurements reported in the examples below, that the area of spreading of a perfume influences the tenacity of the fragrance, in particular, of the more volatile compounds. It is important to mention here that, contrary to the prior art disclosures related to the use of fixative ingredients and which are all based on uses of specific active compounds, with specific interactions with the perfuming ingredients, the technical effect claimed in the present invention, namely the decreasing of the spreading area of the perfume solution when applied on a surface, is not linked to the particular chemical nature of the single polymer used for the purpose of the invention. For that matter, the example below renders obvious the fact that the same technical effect is obtained with single polymers of a great variety of chemical natures.

The invention preferably relates to a transparent, sprayable perfume solution, consisting essentially of from 50 to 99% by weight of ethanol; from 0.5 to 50% by weight of a perfuming ingredient or composition; from 0.5 to 50% by weight of water, and an effective amount of a single polymer selected from the group consisting of a linear or cross-linked (meth-) acrylic acid homo-polymer, a linear or cross-linked (meth-) acrylate copolymer, an ammonium acryloyldimethyltaurate homo- or copolymer and a polyethylene oxide or a derivative thereof, the weight percents being relative to the total weight of the solution.

What is meant here by a perfume solution is a composition based on the presence of alcohol, perfume and water, the alcohol being present in a sufficient amount to solubilize the perfuming ingredient or mixture.

Transparency of a perfume solution is essential for products intended for an application in fine perfumery. The transparency of the solutions of the invention is characterised by a transmission measured at 600 nm in a 1 cm width cell, typically above 80%.

The composition of the invention is fluid, in other words susceptible of being sprayed. In particular its viscosity is typically lower that 10 Pa·s measured at 25° C. and at a shear rate below or equal to 0.001 s$^{-1}$, and the viscosity is lower than 0.15 Pa·s at high shear rate, i.e., typically above 100 s$^{-1}$.

The solution provided by the invention to the problem of tenacity of a perfume when applied onto a surface, advantageously relies on the use of a single ingredient, which is used in an effective amount to decrease the spreading area of the composition when applied on any kind of surface such as glass, skin or other. In other words, the contact area between a droplet of that composition and the solid to which it is applied, is smaller than the same surface measured with a droplet of an identical composition free of the active single polymer mentioned above. Unexpectedly, the reduction of the spreading area of the solution when applied on a surface has the technical effect of slowing down and thus prolonging the diffusion of perfuming ingredients in the air. Besides and advantageously, the presence of said single polymer does not affect neither the sprayability nor the transparency properties of the perfume formulation to which it is added.

The single polymer capable of decreasing the spreading area of a perfume solution when applied on a surface, is selected from the group consisting of a linear or cross-linked (meth-) acrylic acid homo-polymer, a linear or cross-linked (meth-) acrylate copolymer, an ammonium acryloyldimethyltaurate homo- or copolymer and a polyethylene oxide or a derivative thereof. In a particular embodiment, this polymer is used in proportions varying between about 0.05 and 1.5% by weight relative to the total weight of the perfume solution. Such polymers are, in particular, known under the tradenames CARBOPOL® (origin: Goodrich) or PEMULEN® (origin: Goodrich). CARBOPOL® polymers are acrylic acid-based polymers that are crosslinked to different levels with a polyalkenyl polyether, while PEMULEN® polymers are acrylic acid-based polymers that are crosslinked to different levels with a C10-C30 alkyl acrylate.

An effective amount of a single polymer suitable for the purpose of the invention advantageously reduces the spreading area of a typical perfume solution, which proved to improve the tenacity of perfuming ingredients. The invention is particularly useful for extending the diffusion from a surface of volatile perfuming ingredients, which constitutes an important advantage in the field of perfumery.

Optionally, the perfume solution of the invention comprises a neutralising agent, in particular when the single polymer is ionic. Examples of suitable neutralising agents for the purpose of the invention include polyoxyethylene (15) cocoamine, isopropanolamine, isopropylamine, diisopropanolamine, triisopropanolamine, diethanolamine, triethanolamine, tromethamine, aminomethyl propanol or tetrahydroxypropyl ethylenediamine. Commercial products are sold under the names of ETHOMEN® C/25 (origin: Akzo Nobel), AMP-95® (origin: Angus), or NEUTROL® TE (origin: BASF).

The perfume solution of the present invention comprises from 0.5 to 50% by weight of a perfuming ingredient or composition. In a particular embodiment, the latter is comprised between 4 and 30% by weight.

The perfuming ingredients which can be used in the present invention, either in the form of a single compound, or in the form of a mixture of perfuming ingredients forming a perfuming composition, are all ingredients commonly used in perfumery. These ingredients shall not be described in greater detail here, as their description cannot be exhaustive and the skilled person is able to choose them using his general knowledge and as a function of the desired olfactory effect. These perfuming ingredients belong to a variety of chemical classes, as varied as alcohols, aldehydes, ketones, esters, ethers, acetates, nitriles, terpenic hydrocarbons, heterocyclic nitrogen- or sulfur-containing compounds as well as essential oils of natural or synthetic origin. Many of these ingredients are furthermore described in reference textbooks such as S. Arctander, Perfume and Flavor Chemicals, 1969, Montclair, N.J., USA, or its more recent versions, or other books of similar nature. The nature of the perfuming ingredients is not an essential parameter of the invention, and the choice of the latter shall be solely dictated by hedonic requirements, i.e., as a function of the fragrance or odorous effect that it is desired.

The perfume solution of the invention can form as such a consumer product, such as a perfume or an eau de toilette, or can also be used in combination with functional ingredients such as ingredients possessing detergent, cleaning, washing, purifying, deodorant, antiperspirant, antibacterial, cosmetic, conditioning or emollient properties thus forming an active base, for the preparation of functional perfumed articles in the body care or home care areas such as deodorants, antiperspirants, hair-care products, hair-sprays or yet air fresheners.

The invention will now be described in greater detail in the following examples, wherein the temperatures are indicated in degrees centigrade and the abbreviations have the usual meaning in the art.

EXAMPLES

The following examples illustrate preferred modes for carrying out the invention.

Example 1

Preparation of Perfume Solutions According to the Invention—Comparative Measurements of Spreading Areas Two perfume solutions according to the invention were prepared from the following formulas:

| Formula 1 | |
| --- | --- |
| Ingredients | Parts by weight |
| CARBOPOL AQUA ®-SF1 [1] | 1.2 |
| ETHOMEN ® C/25 [2] | 3.0 |
| Water | 5.8 |
| Perfume composition [3] | 10.0 |
| Ethanol | 80.0 |
| Total | 100.0 |

[1] cross-linked acrylate copolymer; origin: Goodrich
[2] polyoxyethylene (15) cocoamine; origin: Akzo Nobel
[3] perfume composition:

| Ingredients | Parts by weight |
| --- | --- |
| Zestover [a] | 2.0 |
| Benzyl acetate | 6.0 |
| Styrallyl acetate | 1.5 |
| Neoflorol [b] | 1.5 |
| Methyl anthranilate | 1.0 |
| Vanillin | 2.0 |
| Coumarine | 1.0 |
| LILIAL ® [c] | 10.0 |
| BACDANOL ® [d] | 1.0 |
| HEDIONE ® [e] | 35.0 |
| CETALOX ® [f] | 2.0 |
| HABANOLIDE ® [g] | 2.0 |
| Benzyl salicylate | 35.0 |
| Total | 100.0 |

[a] 2,4-dimethyl-3-cyclohexen-1-carbaldehyde
[b] (+−)-tetrahydro-2-isobutyl-4-methyl-4(2H)-pyranol
[c] 3-(4-tert-butylphenyl)-2-methylpropanal
[d] 2-ethyl-4-(2,2,3-trimethyl-3-cyclopenten-1-yl)-2-buten-1-ol; origin: International Flavors and Fragrances, USA
[e] methyl dihydrojasmonate; origin: Firmenich SA, Geneva, Switzerland
[f] 8,12-epoxy-13,14,15,16-tetranorlabdane; origin: Firmenich SA, Geneva, Switzerland
[g] pentadecenolide; origin: Firmenich SA, Geneva, Switzerland

| Formula 2 | |
| --- | --- |
| Ingredients | Parts by weight |
| HOSTACERIN AMP ® [1] | 0.7 |
| Diisopropanolamine [2] | 0.1 |
| Water | 19.2 |
| Perfume composition [3] | 10.0 |
| Ethanol | 70.0 |
| Total | 100.0 |

[1] ammonium polyacryloyldimethyltaurate polymer; origin: Clariant
[2] origin: Firmenich SA, Geneva, Switzerland
[3] see Formula 1

For purpose of comparison, a reference solution was prepared from the following formula:

| Blank formula | |
| --- | --- |
| Ingredients | Parts by weight |
| Water | 10.0 |
| Perfume composition [1] | 10.0 |
| Ethanol | 80.0 |
| Total | 100.0 |

[1] see Formula 1

Figure 1:
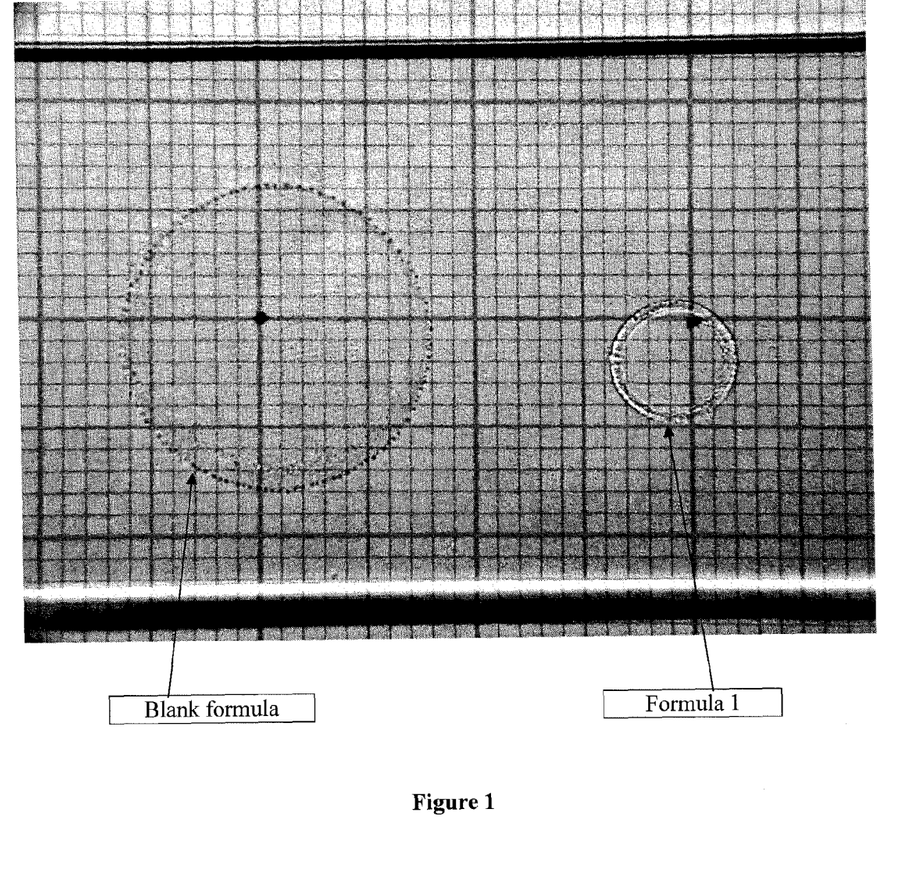
FIG. 1 is a picture showing the modification of the wetting or spreading area of an eau de toilette applied on a glass surface, when the solution comprises a single polymer according to the invention, by comparison with a solution free of polymer.

With the help of a pipette, 2 µl of formula 1, respectively 2 µl of blank formula, were deposited on a glass surface, laid down on a paper with millimeter scale. FIG. 1 shows a picture of the result, wherein the spreading areas have been defined with a pencil. It appears on that figure, that the addition of the polymer in formula 1 caused the decrease of the spreading area of the perfume solution when applied on a glass surface.

Figure 2:
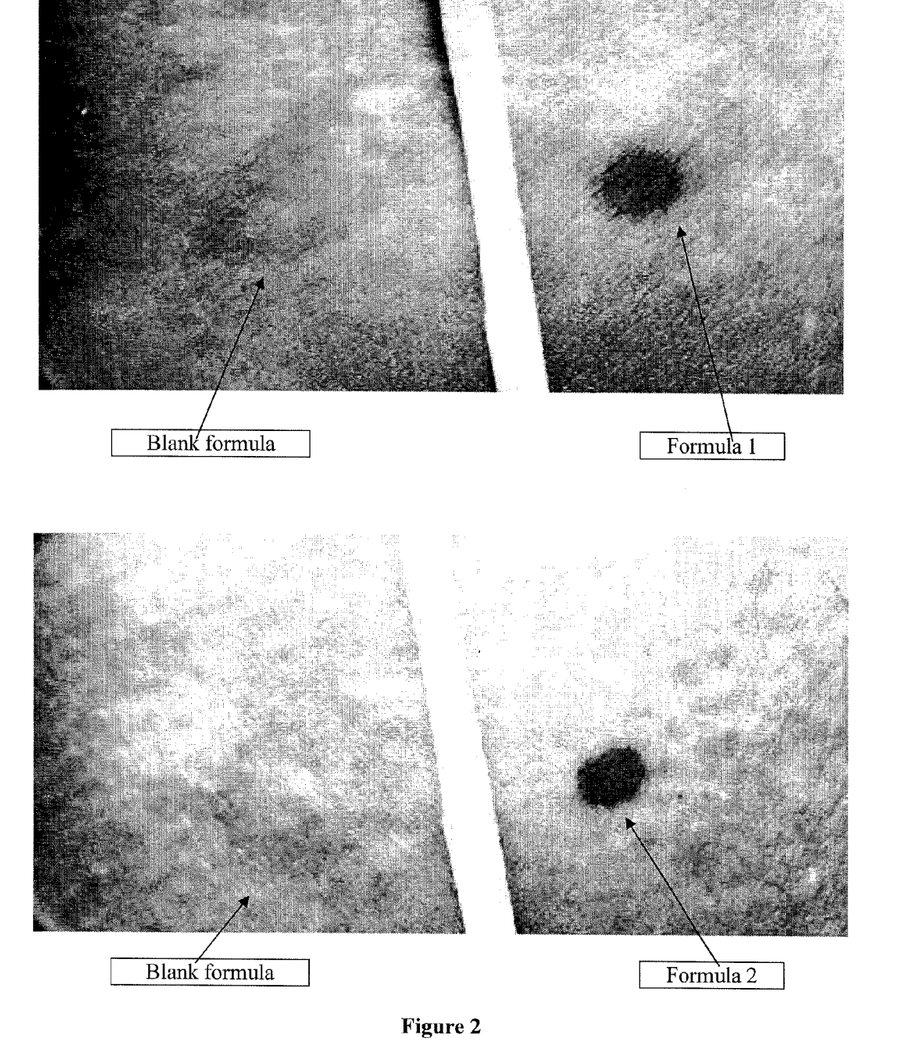
FIG. 2 consists of two pictures comparing the spreading areas of an eau de toilette applied on the skin, when it comprises a single polymer according to the invention, and when it is free of such a polymer.

Similarly, FIG. 2 consists of pictures reporting formula 1 and formula 2 by comparison with a blank formula, during an application of 2 µl of the mentioned solutions on the skin. Both pictures show the difference existing between the spreading areas of solutions with or without the presence of the polymer. The spreading area of the perfume solution according to the invention was reduced from 4 to 5 times by comparison with a perfume solution free of a suitable polymer.

Example 2

Headspace Analysis from Glass or Skin of Solutions of the Invention

General Protocol for a Headspace Analysis

Using a micro-syringe, 2 µl of an eau de toilette of formula 1, respectively formula 2, and blank formula, have been deposited on a glass surface rinsed beforehand with ethanol, or on the inner in-vivo forearm skin of a panellist.

The collection of the molecules of perfume release in air have been performed by dynamic headspace. Air is passed through a collecting cell and adsorbed onto TENAX® cartridges. Collections have been carried out during 15 min for the first point, and for 1 h at $t_{15\,min}$, $t_{1h15}$, $t_{2h15}$, $t_{3h15}$ and $t_{7h}$. Accounting for practicability, reproducibility and reliability worries, the collections have been performed only during 4 h on skin.

The perfume quantity in air is estimated by thermic desorption of the TENAX® cartridges on a Perkin Elmer ATD400 system and analysis by gas chromatography.

Figure 3A:
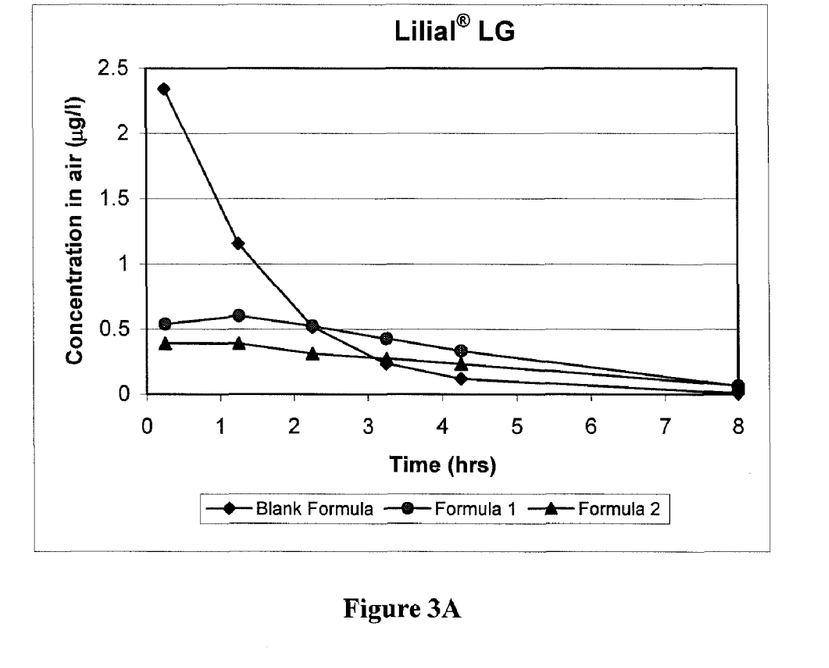
FIGS. 3A and 3B represent headspace results for the evaporation of neoflorol ((+−)-tetrahydro-2-isobutyl-4-methyl-4(2H)-pyranol), respectively Lilial® (3-4(tert-butylphenyl)-2-methylpropanal; origin: Givaudan-Roure, Vernier, Switzerland) from a glass surface, comparing perfume solutions of the invention with a solution free of a polymer capable of reducing its spreading area when applied on a surface.
Figure 3B:
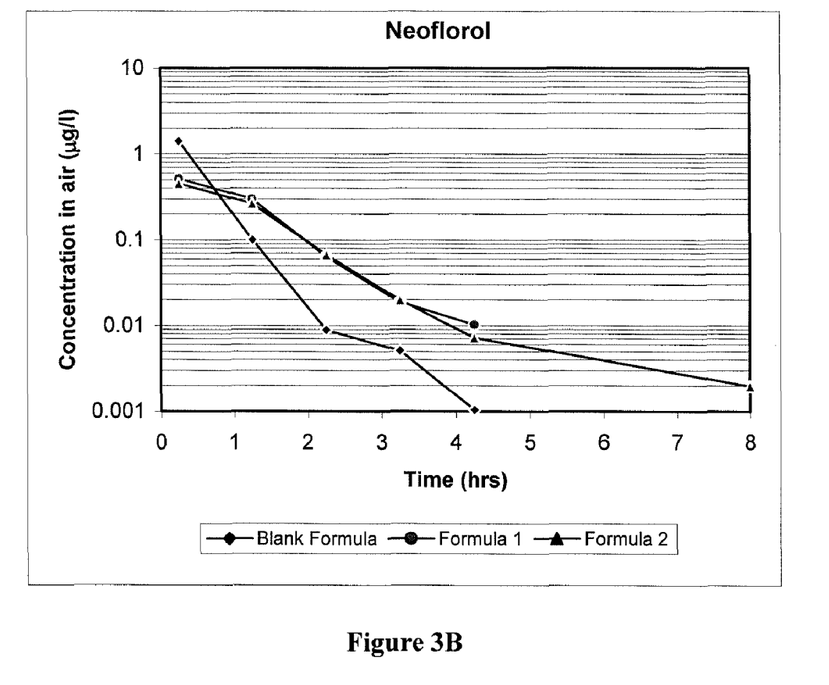

FIGS. 3A and 3B report the headspace analysis that has been performed for Neoflorol ((+−)-tetrahydro-2-isobutyl-4-methyl-4(2H)-pyranol) on the one hand, and LILIAL® (3-(4-tert-butylphenyl)-2-methylpropanal) on the other hand, when formula 1, formula 2 and blank formula respectively, have been deposited on a glass surface.

It is shown that the blank formula profile is very different from that of formulas 1 and 2, which are opposite, very similar. The presence of a single polymer in formulas 1 and 2 clearly allows to extend the diffusion during the time of both analysed compounds, apart from their difference of volatility.

Figure 4A:
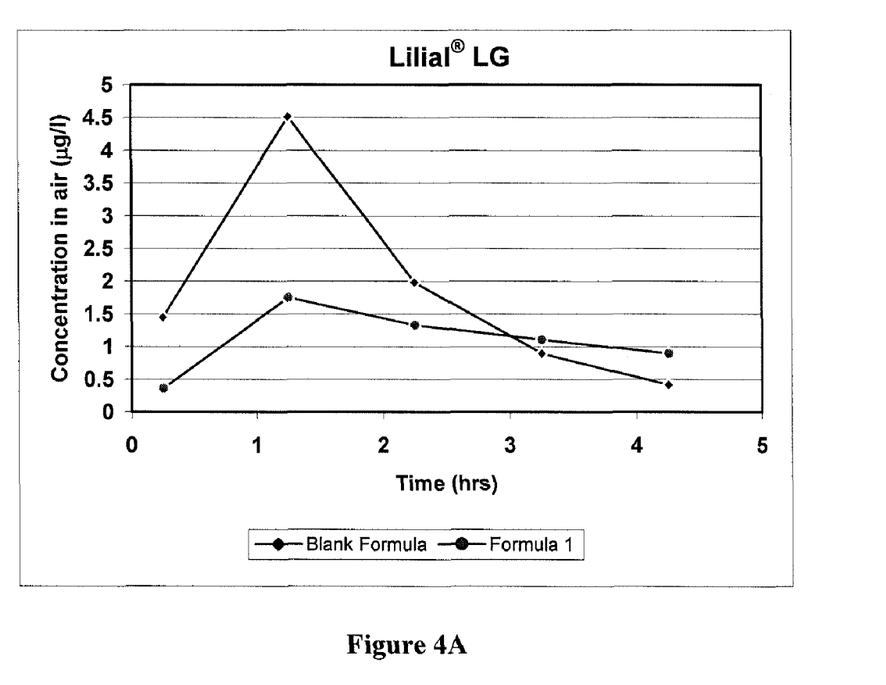
FIGS. 4A and 4B represent headspace results for the evaporation of neoflorol, respectively Lilial® (3-4(tert-butylphenyl)-2-methylpropanal; origin: Givaudan-Roure, Vernier, Switzerland) from the skin, comparing a perfume solution according to the invention with a solution free of a polymer capable of reducing its spreading area when applied on a surface.
Figure 4B:
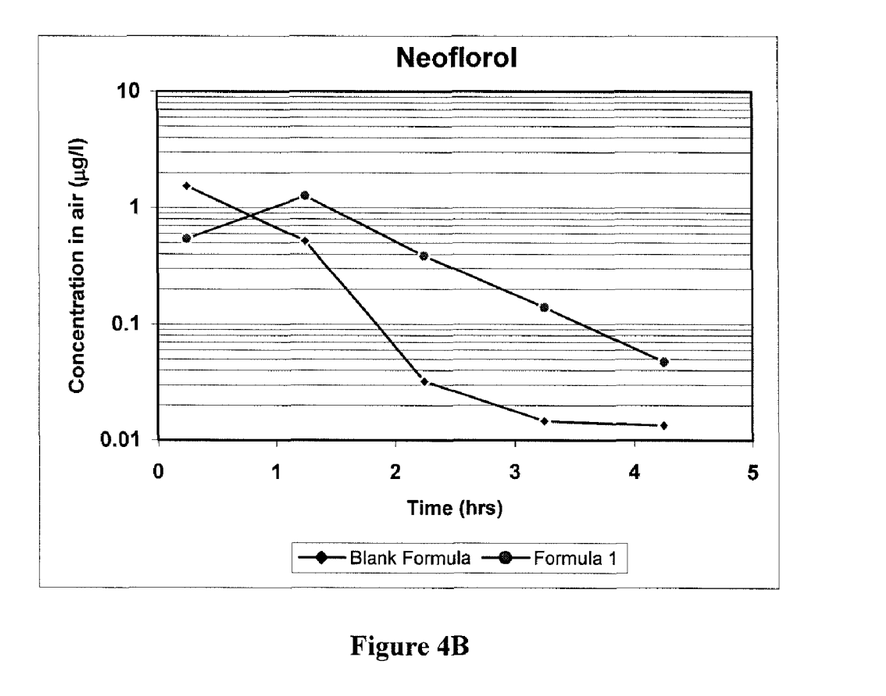

FIGS. 4A and 4B report the headspace analysis that has been performed for Neoflorol ((+−)-tetrahydro-2-isobutyl-4-methyl-4(2H)-pyranol) on the one hand, and LILIAL® (3-(4-tert-butylphenyl)-2-methylpropanal) on the other hand, when formula 1 and blank formula, respectively, have been deposited on the skin. The profile show again a more linear release of perfuming ingredients from formula 1 when compared to the blank formula, inducing a higher concentration of perfume in the air after 1 h in the case of Neoflorol and after more than 3 h in the case of LILIAL®. The solution according to the invention thus allows to extend the diffusion in the air of these perfuming ingredients.

Example 3

Sensorial Analysis of the Intensity of a Perfume in a Solution of the Invention

Formula 1 and blank formula as described in Example 1 were used to conduct a sensorial panel. More particularly, with the help of a pipette, 10 µl of formula 1, respectively 10 µl of blank formula, were deposited on the forearm of 20 panellists. Each panellist then judged the intensity of the perfume after respectively 5 min, 1 h, 2 h, 4 h and 8 h, on a scale of 0 (no intensity) to 10 (maximum of intensity).

Figure 5:
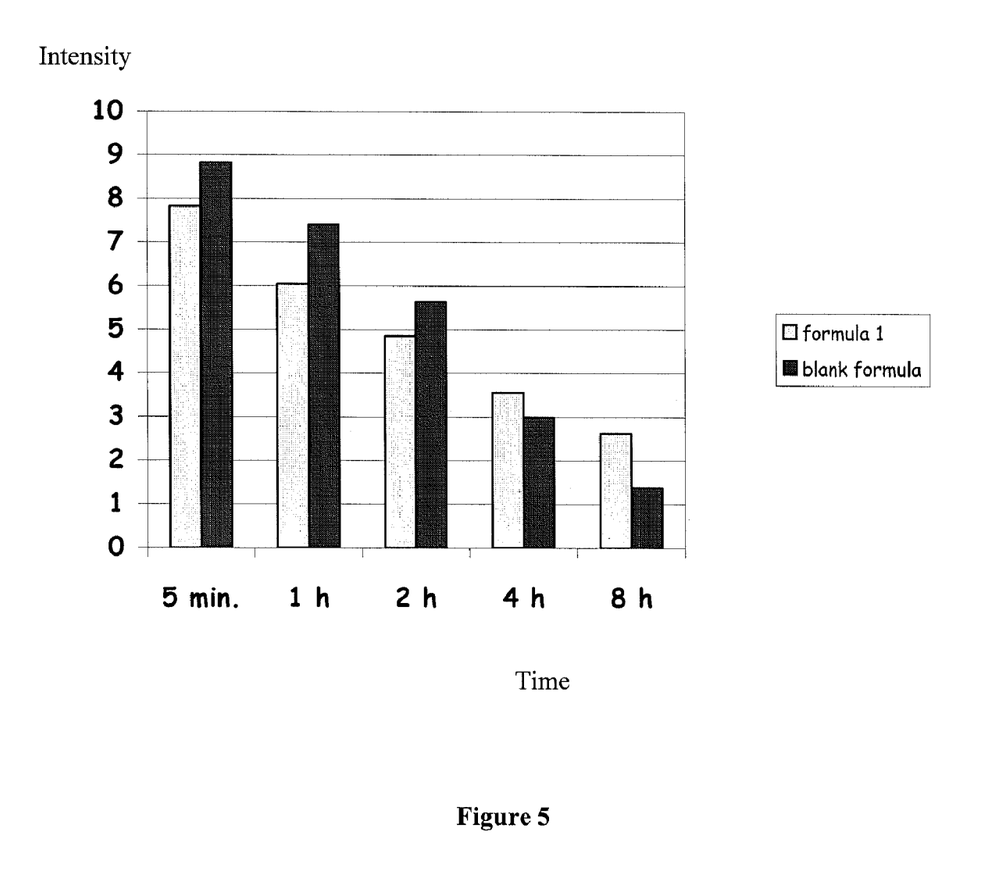
FIG. 5 reports the results of a sensorial analysis and shows the intensity of a perfume evaluated on a 0 to 10 scale by panellists as a function of time, comparing a perfume solution according to the invention with a solution free of a polymer capable of reducing its spreading area when applied on a surface.

The results of the analysis appear on FIG. 5 which reports the mean intensity after a certain time, for each solution. It appeared that 16 of the 20 panellists found that the intensity of the perfume was perceived stronger in the solution according to the invention, namely formula 1, than in the blank formula, after 4 to 8 h applied on the skin. This demonstrates the improvement of the tenacity of a perfume in a perfume solution according to the invention.

What is claimed is:

1. A transparent sprayable perfume solution, consisting of:
    a) from 50 to 99% by weight of ethanol;
    b) from 4 to 30% by weight of a perfuming ingredient or composition;
    c) from 0.5 to 50% by weight of water; and
    d) from 0.05 to 1.5% by weight of a single polymer selected from the group consisting of a linear or cross-linked (meth-) acrylic acid homo-polymer, a linear or cross-linked (meth-) acrylate copolymer, an ammonium acryloyldimethyltaurate homo- or copolymer and a polyethylene oxide or a derivative thereof;
    wherein all percentages are relative to the total weight of the solution.

2. The perfume solution according to claim 1, wherein the perfuming ingredient or composition is present in an amount of 10% by weight, relative to the total weight of the solution.

3. A process for extending the diffusion of a perfume, which comprises applying onto a surface the sprayable perfume solution comprising 50 to 99% by weight of ethanol, 4 to 30% by weight of a perfuming ingredient or composition, 0.5 to 50% by weight of water, and from 0.05 to 1.5% by weight of a single polymer selected from the group consisting of a linear or cross-linked (meth-) acrylic acid homo-polymer, a linear or cross-linked (meth-) acrylate copolymer, an ammonium acryloyldimethyltaurate homo- or copolymer and a polyethylene oxide or a derivative thereof, wherein all percentages are relative to the total weight of the solution.

4. The process according to claim 3, wherein the surface consists of human skin.

5. The process according to claim 3, wherein the single polymer is present in an amount of from 0.05 to 1.5% by weight relative to the total weight of the solution.

6. A perfumed article comprising a perfume solution according to claim 1 in a bottle, together with an active base comprising one or more ingredients possessing detergent, cleaning, washing, purifying, deodorant, antiperspirant, antibacterial, cosmetic, conditioning or emollient properties.

7. A perfume article comprising a perfume solution according to claim 1 in the form of a perfume, an eau de toilette or a Cologne.

* * * * *